(12) United States Patent
Auxepaules et al.

(10) Patent No.: US 8,114,166 B2
(45) Date of Patent: Feb. 14, 2012

(54) RETENTIVE AND REMOVABLE TRIAL BEARING INSERT

(75) Inventors: Arnaud Auxepaules, Saint-Aubin-sur-Mer (FR); Nicolas Delogé, Douvres-la-Deliverande (FR)

(73) Assignee: Benoist Girard SAS (FR)

( * ) Notice: Subject to any disclaimer, the term of this patent is extended or adjusted under 35 U.S.C. 154(b) by 1472 days.

(21) Appl. No.: 11/325,226

(22) Filed: Jan. 4, 2006

(65) Prior Publication Data

US 2006/0173548 A1   Aug. 3, 2006

(30) Foreign Application Priority Data

Jan. 11, 2005   (GB) .................................. 0500510.3

(51) Int. Cl.
    *A61F 2/32*   (2006.01)
(52) U.S. Cl. .................. 623/22.28; 623/22.29
(58) Field of Classification Search ............... 623/22.19, 623/22.2, 22.28, 22.29
    See application file for complete search history.

(56) References Cited

U.S. PATENT DOCUMENTS

| | | | |
|---|---|---|---|
| 4,135,517 A | 1/1979 | Reale | |
| 4,718,911 A | 1/1988 | Kenna | |
| 4,798,610 A * | 1/1989 | Averill et al. | 623/22.2 |
| 5,062,853 A | 11/1991 | Forte | |
| 5,156,626 A | 10/1992 | Broderick et al. | |
| 5,314,491 A * | 5/1994 | Thongpreda et al. | 623/22.29 |
| 5,888,211 A | 3/1999 | Sanders | |
| 2004/0054421 A1* | 3/2004 | McLean | 623/23.11 |
| 2005/0060040 A1 | 3/2005 | Auxepaules et al. | |
| 2005/0075736 A1* | 4/2005 | Collazo | 623/20.16 |

FOREIGN PATENT DOCUMENTS

FR  2 785 525   11/1998

OTHER PUBLICATIONS

European Search Report, E 06 25 0101, Dated, May 10, 2006.

* cited by examiner

*Primary Examiner* — David Isabella
*Assistant Examiner* — Joshua Levine
(74) *Attorney, Agent, or Firm* — Lerner, David, Littenberg, Krumholz & Mentlik, LLP

(57) ABSTRACT

A retentive and removable trial bearing insert is used with a total hip replacement joint. The joint includes a dual mobility or bipolar prosthetic cup which has a part-spherical bearing insert with a part-spherical inner bearing surface which engages a part-spherical bearing head on a femoral stem. The bearing comprises a part-spherical trial inner bearing element dimensioned to replace the part-spherical bearing insert and which includes releasable retaining element which engages the bearing head of the femoral stem or a trial bearing head thereof to hold the trial bearing element in place thereon.

12 Claims, 3 Drawing Sheets

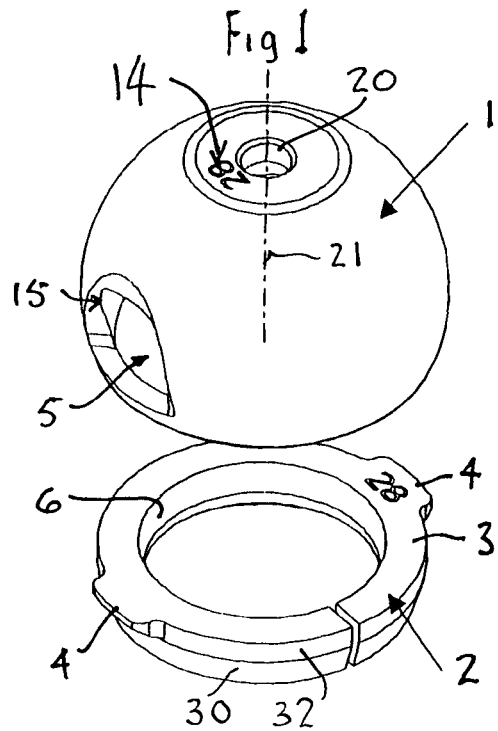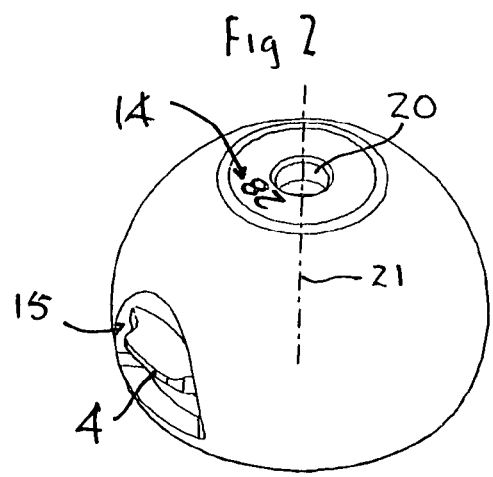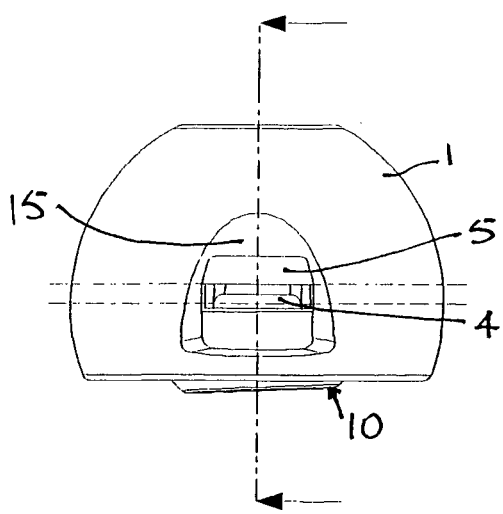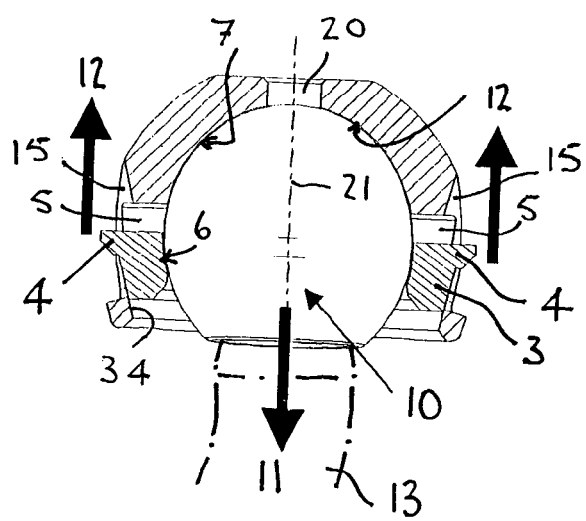

RETENTIVE AND REMOVABLE TRIAL BEARING INSERT

BACKGROUND OF THE INVENTION

This invention relates to a retentive and removable trial bearing insert for use with a total hip replacement joint which includes a dual mobility prosthetic cup and a total hip replacement joint including such a trial bearing insert.

Bipolar cups are well known and have the spherical bearing head of the stem rotatable within the inner surface of an outer bearing having an outer surface which, in turn, rotatably engages the natural acetabulum. Such are shown in U.S. Pat. Nos. 4,798,610 and 5,062,853.

Dual mobility cups, sometimes referred to as tripolar cups, include a part-spherical bearing insert with a part-spherical bearing surface which engages a part-spherical inner bearing head on a femoral stem in a bipolar cup. In addition the bearing insert has an outer bearing surface which is freely movable in an outer cup, usually metallic, which may be fixed to the acetabulum~ Prosthetic cups of this kind are used to provide a greater range of relative movement between the ball head on the femoral stem and the outer cup of the prosthesis.

Dual mobility cups of this type are well known and a dual mobility cup construction is described, for example, in U.S. Patent Publication No. 2005/0060040.

In cups of this type the ball head is "constrained" in that it can be maintained in place in the insert by means of a ring or by a deformation of the insert itself when inserting the head due to the inner diameter of an insert being smaller than the diameter of the head. This type of system is sometimes referred to as an anti-dislocation system because it is harder to dislocate a big head than a smaller one. As mentioned above, this system also offers a wide range of motion because of the rotation of the insert.

When a surgeon puts a total hip replacement joint in place in the patient the ball head which is mounted on a femoral stem is put in place in the femur and the definitive cup is installed in the patient's hip but the surgeon needs trial reduction to check the leg length and the stability of the joint. The surgeon usually prefers to use trial instruments, that is a trial ball head and a trial bearing insert. The problem with dual mobility cups is that if a trial bearing insert is employed there appears to be only the type of device shown in FR 2 785 525 to make inserting and removal of the ball head easy but this requires a specially shaped ball head, and is intended for use with an outer cup not a dual mobility cup.

The present invention is intended to provide a construction of a retentive and removable trial head and bearing insert for use in bipolar and dual mobility cups.

SUMMARY OF THE INVENTION

According to the present invention a retentive and removable trial bearing insert for use with a total hip replacement joint which includes a dual mobility prosthetic cup which has a part-spherical bearing insert with a part-spherical inner bearing surface which engages a part-spherical bearing head on a femoral stem, comprises a part-spherical trial inner bearing element dimensioned to replace the part-spherical bearing insert and which includes releasable retaining element which engage the bearing head of the femoral stem or a trial ball thereof to hold the trial element in place thereon.

Thus, the surgeon can now make up an assembled cup for trial purposes either on the ball head of the femoral stem or on a trial ball head which may have been used for trial purposes. Due to the fact that the trial bearing insert is retentive the surgeon can operate more efficiently and can subsequently remove the trial bearing insert when required.

Preferably the releasable retaining element includes operating means which extend through the wall of the trial bearing element for external operation. This ensures that the surgeon can easily remove the trial bearing insert when he has made his examination.

The releasable retaining element can be arranged to engage the ball or trial ball at a location diameter which is less than the maximum diameter thereof. Thus, the element, in effect, engages behind the maximum diameter of the ball or trial ball.

The releasable retaining element may conveniently comprise a resilient retaining ring located within the part-spherical inner bearing surface of the trial bearing element with operating means projecting radially through the wall thereof for external operation.

With this type of construction the releasable retaining element may comprise a pair of diametrically disposed operating members which project through the wall of the trial bearing element, and the wall of the trial bearing element can be recessed in the area of the operating members so that they can be more easily operated by the surgeon. The design can also be used in a trial of a bipolar cup, i.e. one used without the outer shell coupled to the acetabulum but moveable on the natural acetabulum itself.

Also included in the invention is a retentive and removable trial bearing insert as set forth above which, in combination therewith, a dissembling tool which comprises a base with a projecting stem which is adapted to be passed through an opening in the trial part-spherical bearing element to dislodge the bearing head of the femoral stem in a direction to disengage it therefrom.

In a preferred construction the dissembling tool is incorporated in an instrument tray.

The invention also includes a retentive trial bearing insert or retentive trial bearing insert in combination with a dissembling tool as set forth above, in combination with a total hip replacement joint which includes a dual mobility or bipolar prosthetic cup which has a part-spherical bearing insert with a part-spherical inner bearing surface which engages a part-spherical inner bearing femoral stem and which is adapted to be replaced by said trial bearing insert.

These aspects of the invention are achieved by a retentive and removable trial bearing insert for use with total hip replacement joint which has a prosthetic femoral implant with a modular spherical or ball-shaped head. The acetabular side of the total hip replacement joint includes a dual mobility or bipolar, or tripolar prosthetic cup which has a part-spherical outer bearing surface and a part-spherical inner bearing surface which engages the part-spherical bearing head in the femoral stem. The trial bearing insert includes a part-spherical trial inner bearing element dimensioned to replace the part-spherical bearing insert and which includes an inner portion with a retaining element which engages the bearing head of the femoral stem or a trial bearing head on the femoral stem to the hold the trial bearing element thereon.

The removable retaining element includes actuating lugs which extend through the wall of the trial bearing element which lugs can be grasped by the surgeon to release the insert from the head. The releasable retaining element, which is in the form of a split-ring, engages the bearing head or trial bearing head at a diameter thereon, which is less than the maximum diameter thereof. The releasable retaining element comprises a resilient retaining ring located within the part spherical inner bearing surface of the trial bearing element with the operating lugs projecting radially through the wall for external operation. In a preferred embodiment, the lugs are diametrically opposed and project through diametrically opposed openings in the trial bearing element walls. The wall of the trial bearing element is recessed on the outer surface toward the inner surface in the area with the openings for the lugs.

A disassembling or removal tool is provided which comprises a base with a projecting stem which is adapted to be inserted through a polar opening in the trial part-spherical bearing element to dislodge the bearing head of the femoral stem in a direction to disengage it from the insert. The disassembling tool can be included in an instrument tray on which the trial inserts are provided.

BRIEF DESCRIPTION OF THE DRAWINGS

The invention can be performed in various ways but one embodiment will now be described by way of example and with reference to the accompanying drawings in which:

FIG. 1 is an isometric view of the two parts which comprise the retentive removable trial bearing insert according to the invention;

FIG. 2 is an isometric view of the two-parts of the trial bearing insert shown in FIG. 1 assembled together;

FIG. 3 is a side elevation of the trial bearing insert according to the invention;

FIG. 4 is a cross-sectional view on the line IV-IV of FIG. 3 assembled to the ball head of a prosthetic stem;

DETAILED DESCRIPTION

Figure 5:
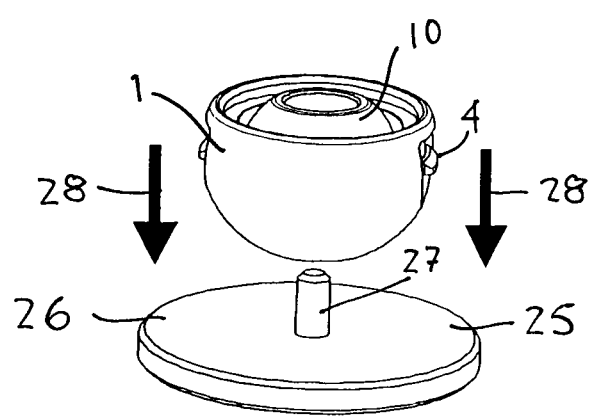
FIG. 5 is an isometric view showing how a disassembling tool can be used to release a ball head.

Referring to FIGS. 1-4, there is shown a retentive removable trial bearing insert for use with a total hip replacement joint, which includes a dual mobility prosthetic cup having an outer shell coupled to the acetabulum (not shown) and which has a part-spherical bearing insert with a part-spherical inner bearing surface which engages a part-spherical bearing head on a femoral stem. The bearing comprises a part-spherical trial inner bearing element indicated by reference numeral 1. Bearing element 1 is dimensioned to replace the part-spherical bearing insert of the dual mobility cup with which it is to be used. Preferably, bearing element 1 has a part-spherical outer surface to contact the inner spherical bearing surface of the outer cup during the trialing procedure. The trial inner bearing element 1 is held in place on the ball head of the joint by a releasable retaining element 2 and which comprises a resilient split retaining ring 3. Operating means are provided by a pair of diametrically disposed operating members 4 which are in the form of lugs which, when the ring is assembled in the element 1, project through openings 5 in the inner bearing surface 6 on the inner wall of the part-spherical element 1. The assembled construction is most clearly shown in FIG. 4. While in the preferred embodiment two openings 10 are provided one or more than two can be used.

The preferred retaining ring 3 has an inwardly conically tapered surface 30 below a rim 32 from which lugs 4 extend. Tapered surface 30 is adapted to engage tapered surface 34 at the base of bearing insert 1. These surfaces allow split ring 3 to expand upon upward movement of the ring within insert 1. Preferably ring 3 is assembled within insert 1 during manufacture.

The inner surface 6 of retaining ring 2 is shaped to conform to the shape of the ball, indicated by reference numeral 10 in FIG. 4, and the ring is located within the part-spherical inner bearing surface 7 of the element 1 at a location diameter which is less than the maximum diameter thereof. As shown in FIG. 4 resilient ring 3 has retained its natural shape and thus holds trial element 1 in position on the ball 10. The size and location of lower openings 5 allow for the up and down movement of lugs 4 from a lower position opposite where the tapered surfaces collapse ring 3 to an inner diameter smaller than the maximum ball head 10 diameter to an upper position where ring 3 can expand to an inner diameter greater than the ball head maximum diameter. When at its lower point in opening 5 lugs 4 do not project beyond the outer surface of bearing 1.

The trial element is easily pushed onto the ball head 10 in the direction of the arrow 11 by the split ring 3 expanding due to its resilience. When it is necessary to remove trial bearing element 1 it is merely necessary for the surgeon to pull upwards in the direction of the arrows 12 on each of the lugs 4 which assists in deforming ring 2 outwardly to allow it to disengage from head 10.

Head 10 can be a trial head secured on the neck 13 of the stem or it could be the intended head for the stem 13 or, alternatively, the stem 13 and head 10 could be trial members.

As the surgeon can be supplied with a number of trial bearing elements they can be marked appropriately with, for example, the diameter, as indicated by reference numeral 14.

In the construction shown in the drawings the area of the outer wall of the element 1 where the operating members 4 project through it are recessed, as indicated by reference numeral 15, to assist in their operation.

The resilient spring retaining ring can be made of any suitable material, for example a synthetic plastics material or metal.

Due to the construction of the present invention it can be easily dissembled for cleaning and sterilization.

The force required to connect the insert to the ball head is relatively low but the extraction force is higher but can be accommodated by the use of the lugs 4.

Figure 6:
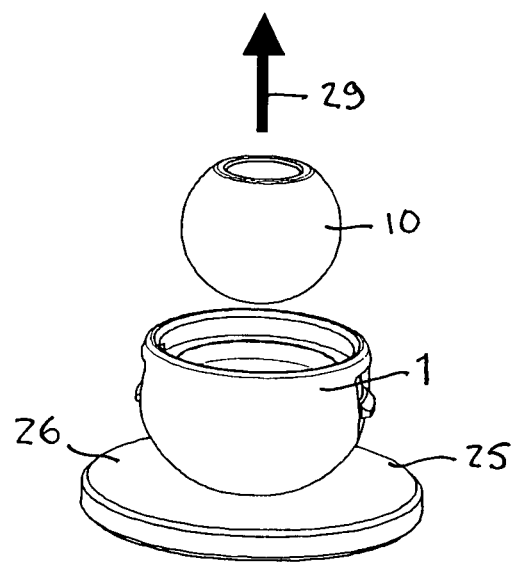
FIG. 6 shows the ball head released from the trial part-spherical inner bearing element using the disassembling tool shown in FIG. 5; and, FIG. 7 is a diagrammatic isometric view from above of an instrument tray incorporating the dissembling tool.

FIGS. 5 and 6 show how a disassembling tool can be employed with the retentive removable trial bearing insert according to the invention and as shown in FIGS. 1 to 4.

As will be seen from FIGS. 1 to 4 the part-spherical trial inner bearing element 1 is provided with a bore or opening 20 on its main or polar axis 21 which is substantially aligned with the axis of the inner bearing surface 6 on the inner wall of the element 1.

This opening 20 is utilized to receive disassembling tool 25 which comprise a circular flat base 26 and a projecting stem 27. The disassembling tool 25 can be used to more easily remove the ball 10 from the part-spherical trial inner bearing element I by placing element 1 on the stem 27 of disassembling tool 25 so that the stem projects through the opening 20 and engages the surface of the ball 10. Pressure applied to the base 26 now causes the walls of the ball 10 to expand the resilient split retaining ring 3 enabling the ball to be removed. Removal is assisted by the surgeon pushing downwardly in the direction of arrows 12 on each of lugs 4.

The base 26 can either be pushed inwards by the surgeon's hand or it can be placed on a flat surface and the part-spherical trial inner bearing element 1 complete with ball 10 pushed downwardly onto it, as shown in FIG. 5, the downward movement being indicated by the arrows 28. FIG. 6 shows how ball 10 is pushed upwardly in the direction of the arrow 29 out of element 1 while lugs, and thus ring 3, are held downward in its expanded position.

The disassembling tool 25 can be made from any suitable material, for example metal or a synthetic plastics material.

Figure 7:
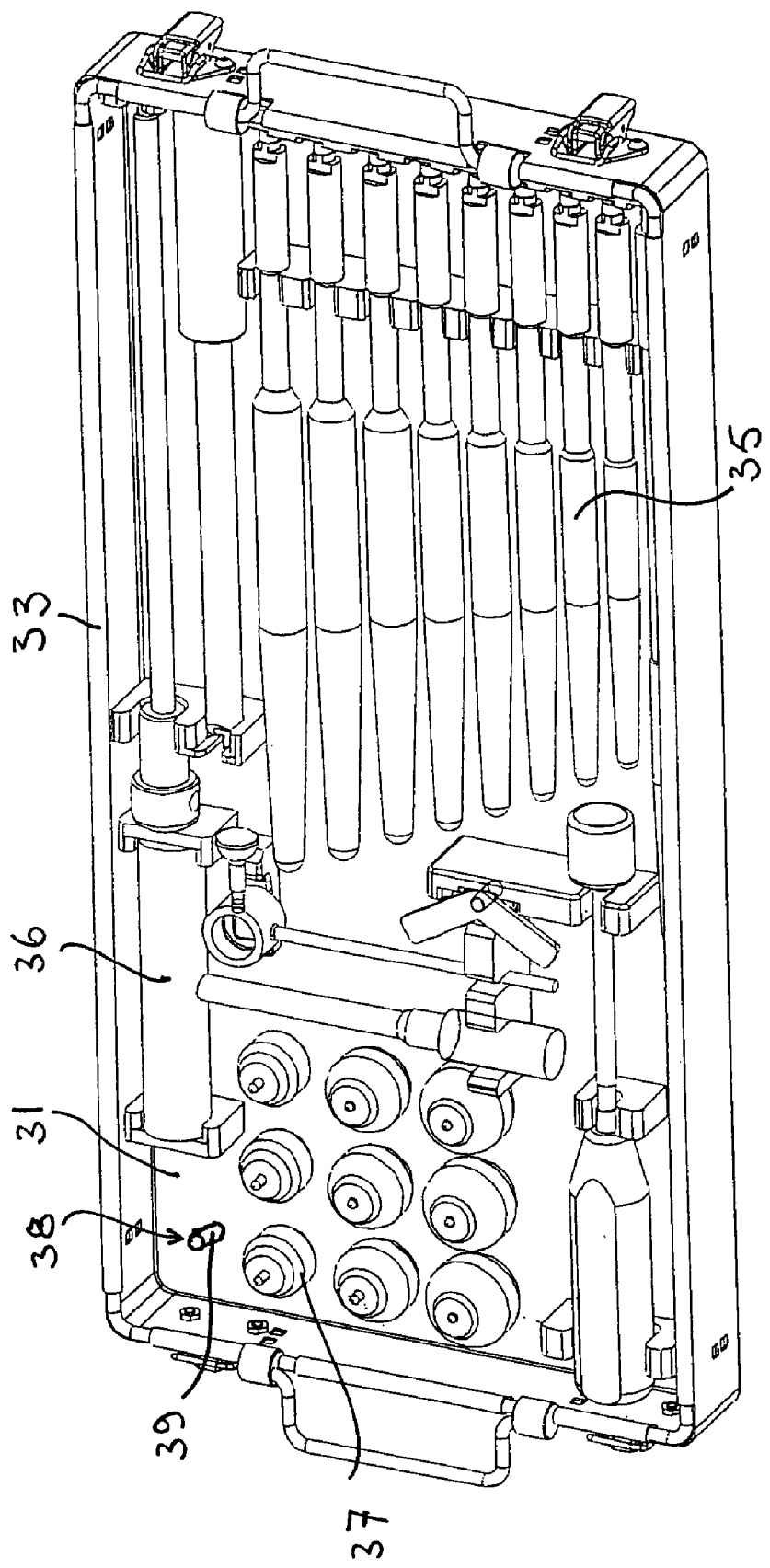

FIG. 7 shows an instrument tray or kit incorporating the dissembling tool. Instrument bays are used to carry a collection of instruments and parts which are used during surgery. They can be supplied by the manufacturers to carry all the instruments required for a particular operation or they can be made up by the surgeon himself as required. The trays, supplied by the manufacturers, are provided with particular locations and fixtures to carry the particular Instruments concerned and they often also have means to carry, for example, prosthesis parts which am to be used. Such trays frequently come as a tray with side walls and a removable lid.

The tray shown in FIG. 7 has upturned sides 30 and a lower base 31 on which are provided preset location positions and retainers to carry some of the Instruments required to perform the appropriate surgery to install and act on the trial bearing inserts according to the Invention. Thus, the tray carries a graduated series of rasps 35, a T-shaped handle for rasps 36 and other appropriate instruments. It also carries nine trial bearing inserts of different sizes and these are indicated by reference numeral 37.

Mounted on base 31 of the tray is dissembling tool 38 for use as described above. The dissembling tool comprises an upwardly projecting stem 39 which is rigidly secured to base 31 of the tray. The upwardly projecting stem 39 can be used in a similar manner to stem 27 described above.

The base 31 of the tray provides a convenient location for stems 39 and ensures that it is not a loose component which could be lost or not be to hand when required.

The invention provides apparatus which can be easily dissembled and achieves the requirement of surgeons for a retentive trial bearing insert.

In the construction described above the invention is shown in use with a dual mobility prosthetic cup but it can also be employed with the trial of a bipolar cup in a similar manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A retentive and removable trial bearing insert for use with a total hip replacement joint which includes a dual mobility or bipolar prosthetic cup which has a part-spherical outer bearing with a part-spherical inner bearing surface which engages a part-spherical bearing head on a femoral stem comprising a part-spherical trial inner bearing element dimensioned to replace the part-spherical bearing insert and which includes an outer bearing surface and an inner bearing portion defining a wall there between the wall having a pair of diametrically opposed openings and an expandable retaining element mounted within the inner bearing portion having an outer tapered surface, an inner surface of the wall having a recessed circumferential tapered portion tapered outwardly from an open end of the trial bearing insert and the expandable retainer insert having two lugs with one lug extending through each opening of the pair of openings in the wall which expandable retaining element has an inner surface which engages the bearing head of the femoral stem or a trial bearing head thereof to hold the trial bearing element beyond the outer bearing surface in place thereon, said expandable retaining element lugs extend through the openings in the wall of the trial bearing element for external operation and are moveable within each opening in the wall in an axial direction of the part-spherical trial inner bearing element from a first contracted position to a second expanded position, said expandable retaining element has an inner surface in the first contracted position which engages said bearing head or trial bearing head at a diameter which is less than the maximum diameter thereof and the inner surface in the expanded position has a diameter greater than the maximum diameter of the head and is spaced from the head.

2. The retentive and removable trial bearing insert as claimed in claim 1 in which said expandable retaining element comprise a resilient retaining ring located within the part-spherical inner bearing surface of said trial bearing element with lugs projecting radially outwardly through the openings in the wall thereof for external operation.

3. The retentive and removable trial bearing insert as claimed in claim 2 in which the lugs comprise a pair of diametrically disposed operating members which project outwardly through the wall of the trial bearing element a distance sufficient for gripping by a surgeon.

4. The retentive and removable trial bearing insert as claimed in claim 3 in which the tapered inner surface of the wall of the trial bearing element is recessed in an area around the opening in the wall of the part-spherical bearing insert.

5. The retentive and removable trial bearing insert as claimed in claim 1 wherein the bearing insert has an aperture centered around a polar axis and which includes in combination therewith a dissembling tool comprising a base with a projecting stem which is adapted to be passed through the aperture in the trial part-spherical bearing element to dislodge the bearing head of a femoral stem in a direction to disengage from the insert.

6. The retentive and removable trial bearing insert as claimed in claim 5 which includes in combination therewith a disassembling tool in which said disassembling tool is incorporated in an instrument tray.

7. A trial bearing insert for a bipolar or tripolar acetabular cup comprising:

a part spherical outer bearing surface and a part-spherical inner bearing surface for receiving a part-spherical head of a hip implant; said surfaces defining a wall therebetween with a pair of openings in said wall, an inner surface of the wall having a circumferential portion tapered outwardly; and a circular split-ring resiliently mounted within said insert, said split-ring having an inner surface and an outer tapered surface and two lugs with one lug extending through one of said pair of openings beyond the outer bearing surface, said openings in said wall allowing the split ring to be moveable within each opening in the wall in an axial direction along the inner tapered surface of the wall from a first axial position with respect to the open end of the trial bearing insert to a second axial position with respect to the open end wherein said bearing insert tapered inner wall surface is an outwardly conically tapered surface adjacent an open end of said bearing insert and the split ring outer tapered surface is a conically tapered surface which tapered surfaces are in sliding engagement in the axial direction from the first to the second axial position, said releasable retaining element inner diameter engages said part-spherical head at a diameter which is less than the maximum head diameter thereof when in the first axial position and opens to a diameter larger than the maximum head diameter in the second axial position and is spaced from the head.

8. The trial bearing insert of claim 7, wherein an outer surface surrounding said opening in said wall of said insert is recessed toward said inner surface.

9. The trial bearing insert as set forth in claim 7, wherein said split ring has a part-spherical inner surface for contacting said head of said hip implant.

10. The trial bearing insert as set forth in claim 7, wherein a polar area of said wall between said inner and outer part-spherical surfaces has a bore therethrough.

11. The trial bearing insert as set forth in claim 7, wherein said retaining ring has a pair of diametrically opposed lugs for extension through a pair of diametrically opposed openings in said wall.

12. A retentive and removable trial bearing insert for use with a total hip replacement joint which includes a dual mobility or bipolar prosthetic cup which has a part-spherical outer bearing with a part-spherical inner bearing surface which engages a part-spherical bearing head on a femoral stem comprising a part-spherical trial inner bearing element dimensioned to replace the part-spherical bearing insert and which includes an outer bearing surface and an inner bearing portion defining a wall therebetween, the wall having a pair of diametrically opposed openings having a distal first axial position and a proximal second axial position spaced along an axis and an expandable retaining element mounted on an inner surface of the inner bearing portion, the retaining element having a lug extending through each opening of the pair of openings in the wall, which retaining element has an inner surface which engages the bearing head of the femoral stem or a trial bearing head thereof to hold the trial bearing element in place thereon, in which said expandable retaining element lugs extend through the openings in the wall beyond the outer bearing of the trial bearing element for external operation and are moveable within each opening in the wall in an axial direction along a polar axis of the part-spherical trial inner bearing portion, in which said expandable retaining element inner surface engages said bearing head or trial bearing head at a diameter which is less than the maximum diameter thereof in the first axial position and the inner retaining element surface has a diameter greater than the maximum diameter of the head and is spaced from the head at the second axial position the inner surface of the trial inner bearing portion having a recessed tapered section tapering outwardly on moving along the axis from the distal first axial position to the proximal second axial position of the inner bearing portion and the retaining element having a tapered outer surface for sliding engagement with the tapered inner surface on movement thereof between the first and second axial positions.

* * * * *

UNITED STATES PATENT AND TRADEMARK OFFICE
CERTIFICATE OF CORRECTION

PATENT NO. : 8,114,166 B2
APPLICATION NO. : 11/325226
DATED : February 14, 2012
INVENTOR(S) : Arnaud Auxepaules et al.

It is certified that error appears in the above-identified patent and that said Letters Patent is hereby corrected as shown below:

Column 5, line 64, "trial bearing element beyond the outer bearing surface in place thereon," should read --trial bearing element in place thereon--.

Column 5, line 67, "trial bearing element for external operation" should read --trial bearing element beyond the outer bearing surface for external operation--.

Signed and Sealed this
Ninth Day of April, 2013

Teresa Stanek Rea
*Acting Director of the United States Patent and Trademark Office*